US011072761B2

(12) United States Patent
Post et al.

(10) Patent No.: US 11,072,761 B2
(45) Date of Patent: Jul. 27, 2021

(54) COMPOSITIONS COMPRISING ODORANTS

(71) Applicant: S H KELKAR AND COMPANY LIMITED, Mumbai (IN)

(72) Inventors: Freddy Post, Arnhem (NL); Kedar Ramesh Vaze, Mumbai (IN); Leszek Doszczak, Amersfoort (NL); Andre Scholten, Berghem (NL)

(73) Assignee: S H KELKAR AND COMPANY LIMITED, Mumbai (IN)

( * ) Notice: Subject to any disclaimer, the term of this patent is extended or adjusted under 35 U.S.C. 154(b) by 0 days.

(21) Appl. No.: 16/634,427

(22) PCT Filed: Aug. 2, 2018

(86) PCT No.: PCT/EP2018/071053
§ 371 (c)(1),
(2) Date: Jan. 27, 2020

(87) PCT Pub. No.: WO2019/030122
PCT Pub. Date: Feb. 14, 2019

(65) Prior Publication Data
US 2020/0157461 A1 May 21, 2020

(30) Foreign Application Priority Data

Aug. 8, 2017 (IN) .............................. 201721028138
Oct. 4, 2017 (EP) .................................... 17194760

(51) Int. Cl.
| | |
|---|---|
| *A61K 8/00* | (2006.01) |
| *A61K 8/18* | (2006.01) |
| *A61Q 13/00* | (2006.01) |
| *C11B 9/00* | (2006.01) |
| *A23L 27/20* | (2016.01) |
| *A61L 2/16* | (2006.01) |
| *C07C 29/14* | (2006.01) |
| *C07C 41/01* | (2006.01) |
| *C07C 43/15* | (2006.01) |
| *C07C 45/75* | (2006.01) |

(52) U.S. Cl.
CPC ........ *C11B 9/0015* (2013.01); *A23L 27/2024* (2016.08); *A61L 2/16* (2013.01); *C07C 29/14* (2013.01); *C07C 41/01* (2013.01); *C07C 43/15* (2013.01); *C07C 45/75* (2013.01); *A23V 2002/00* (2013.01)

(58) Field of Classification Search
CPC ......... C07C 43/15; C07C 29/14; C07C 29/40; C07C 45/75; C07C 45/45; C07C 41/01; C07C 41/16; C07C 33/03; C07C 47/21; C11B 9/0015; A23L 27/2024; A61L 2/16; A23V 2002/00
USPC .......................................................... 512/1
See application file for complete search history.

(56) References Cited

U.S. PATENT DOCUMENTS

| | | | |
|---|---|---|---|
| 2,042,219 A | 5/1936 | Groll et al. | |
| 2,518,416 A | 8/1950 | Bortnick | |
| 6,340,666 B1 | 1/2002 | Narula et al. | |
| 2008/0319088 A1* | 12/2008 | Smith | ................... C07C 47/198 |
| | | | 514/693 |

FOREIGN PATENT DOCUMENTS

| | | |
|---|---|---|
| CH | 359437 A | 1/1962 |
| CH | 583035 A5 | 12/1976 |
| CN | 103739445 A | 4/2014 |
| JP | 2016124790 A | 7/2016 |
| WO | 2007063703 A1 | 6/2007 |
| WO | 2008034863 A2 | 3/2008 |

OTHER PUBLICATIONS

La et al, Mo-Catalyzed Asymmertric Synthesis of Dihydrofurans. Catalytic Kinetic REsoution and Enantioselective Desymmetrization through Ring-Closing Methasis, 1998, 120, 9720-9721 (Year: 1998).*
Reuter et al., "Ruthenium(II) Catalyzed Rearrangement of Diallyl Ethers. A Synthesis of gamma, delta-Unsaturated Aldehydes and Ketones", Journal of Organic Chemistry, 1977, p. 3360-3364, vol. 42, No. 21.
Mikami et al., "New sigmatropic sequences based on the [2,3] Wittig rearrangement of bis(allylic) ethers", Journal of Organic Chemistry, 1981, p. 5447-5449, vol. 46, No. 26.
Dauben et al., "Photochemistry of 1, 5-Hexadien-3-ones: Wavelength-Dependent Selectivity in Intramolecular Enone-Olefin Photoadditions", Journal of the American Chemical Society, 1991, p. 5817-5824, vol. 113, No. 15.
La et al., "Mo-Catalyzed Asymmetric Synthesis of Dihydrofurans. Catalytic Kinetic Resolution and Enantioselective Desymmetrization through Ring-Closing Metathesis", Journal of the American Chemical Society, American Chemical Society, US, Jan. 1, 1998, vol. 120.
Steinreiber et al., "Enantioselective hydrolysis of functionalized 2, 2-disubstituted exirans with bacterial epoxide hydrolases", European Journal of Organic Chemistry, 2000, p. 3703-3700, vol. 2000.
Camacho et al., "Palladium-catalyzed addition of alcohol pronucleophiles to alkylidenecyclopropanes", The Journal of Organic Chemistry Jan. 12, 2001, Jan. 12, 2001, p. 270-275, vol. 66, No. 1.
Hodgson et al., "Organolithium-Induced Synthesis of Unsaturated Diols from Epoxides of Dihydrofurans and Dihydropyrans", Synth, Georg Thieme Verlag, Stuttgart, DE, Jan. 1, 2002, p. 1445-1453, No. 10.
Hultzsch et al., "The First Polymer-Supported and Recyclable Chiral Catalyst for Enantioselective Olefin Metathesis", Angewandte Chemie International Edition, Verlag Chemie, Jan. 1, 2002, pp. 589-593, vol. 41, No. 4.

(Continued)

*Primary Examiner* — Jessica Whiteley
(74) *Attorney, Agent, or Firm* — Maschoff Brennan

(57) ABSTRACT

The present invention relates to odorous 2- and/or 3-substituted 3-(allyloxy)propenes which are useful as fragrance or flavor ingredients in particular in providing green, fruity, pear and/or waxy olfactory notes. The present invention also relates to novel perfume, aroma or deodorizing/masking compositions comprising said odorants.

16 Claims, No Drawings

(56) References Cited

OTHER PUBLICATIONS

Gerhard et al., "Cobalt(I)-catalyzed 1,4-Hydrovinylation Reactions of 1,3-Dienes with Functionalized Terminal Alkenes under Mild Conditions", Synthesis, Apr. 8, 2002, p. 609-618, No. 5.
International Search Report dated Dec. 18, 2018 (6 pages).

* cited by examiner

COMPOSITIONS COMPRISING ODORANTS

FIELD OF THE INVENTION

The present invention relates to odorous 2- and/or 3-substituted 3-(allyloxy)propenes (odorants) which are useful as fragrance or flavor materials in particular in providing green, fruity, pear and/or waxy olfactory notes to perfume, aroma or deodorizing/masking compositions. The present invention also relates to fragrance, flavor and/or deodorizing/masking compositions comprising said odorant 2- and/or 3-substituted 3-(allyloxy)propenes. The present invention furthermore refers to the said odorants which can be used in the novel fragrance, flavor and/or deodorizing/masking compositions of the present invention. The present invention also refers to a method for the production of the said odorants/compounds and of the corresponding fragrance, flavor and/or deodorizing/masking compositions containing said odorants/compounds.

BACKGROUND OF THE INVENTION

Typically, many odorants that are presently utilized in the perfumery industry and/or the flavor industry are synthetic molecules. In particular, there is a high demand and need for novel odorants/compounds and/or for novel fragrance, flavor and/or deodorizing/masking compositions comprising said odorants/compounds.

1-(2-propenoxy)-2-tert-butyl-2-propene is cited in the article of J. Am. Chem. Soc. 1991, 113, pages 5817-5824 which relates to a study of the photochemistry of ten 1,5-hexadien-3-ones in methanol over the wavelength range of 313-366 nm, by using monochromatic light. As indicated on page 5822 of this article, 1-(2-propenoxy)-2-tert-butyl-2-propene is recited as an intermediate chemical compound during the preparation of 5-tert-Butyl-1,5-hexadien-3-one (5) from 2,3,3-trimethyl-1-butene. No fragrance, flavor and/or deodorizing/masking compositions are disclosed in this article and there is absolutely no evidence nor any suggestion of the existence of any olfactive property associated with compound 1-(2-propenoxy)-2-tert-butyl-2-propene.

Allyl 2-pentyl allyl ether is cited in the article of Synthesis, Georg Thieme Verlag Stuttgart, DE, 10, 1 Jan. 2002, pages 1445-1453 which relates to a new route to substituted alkenediols by reacting dihydrofuran and dihydropyran epoxides to a stereospecific alkylative double ring-opening with organolithiums. As indicated on page 1449 of this article, Allyl 2-pentyl allyl ether is recited as an intermediate chemical compound during the preparation of substituted alkenediols from trisubstituted epoxide (scheme 7). No fragrance, flavor and/or deodorizing/masking compositions are disclosed in this article and there is absolutely no evidence nor any suggestion of the existence of any olfactive property associated with compound Allyl 2-pentyl allyl ether.

It is an advantage of one or more of the embodiments of the present invention that the odorants/compounds can impart and/or accentuate particular olfactory notes, in particular providing green, fruity, pear and/or waxy olfactory notes to fragrance, flavor and/or deodorizing/masking compositions.

SUMMARY OF THE INVENTION

This invention discloses novel fragrance, flavor and/or deodorizing/masking compositions comprising a 2- and/or 3-substituted 3-(allyloxy)propene of formula (I)

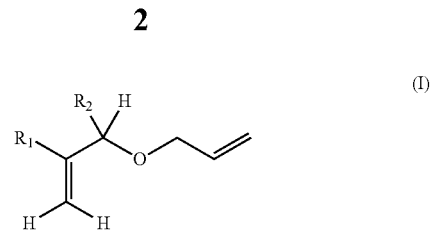

(I)

wherein $R_1$ is either an alkyl group having up to 9 carbon atoms or an alkenyl group having up to 9 carbon atoms and $R_2$ is hydrogen or an alkyl or alkenyl group having up to 5 carbon atoms. In an embodiment according to the present invention, $R_1$ is an alkyl group having up to 5 carbon atoms. In an embodiment according to the present invention, the 2- and/or 3-substituted 3-(allyloxy)propene of formula (I) does not include the compound of formula (I) having a methyl group as $R_1$ and hydrogen as $R_2$. In an embodiment according to the present invention, the 2- and/or 3-substituted 3-(allyloxy)propene of formula (I) comprises at least 8 carbon atoms. In an embodiment according to the present invention, $R_1$ is an alkyl group having at least 2 carbon atoms. For the avoidance of doubt, radicals $R_1$ and $R_2$ are separated radicals, i.e. they do not form together a ring. In another embodiment the compounds of this invention can be chiral, e.g. they can be used as stereoisomeric mixtures, more specifically as mixture of enantiomers; R isomer, S isomer, a racemic mixture and/or a non-racemic mixture of R and S isomers can also be advantageously used.

DETAILED DESCRIPTION

The term "odorant" characterizing the compounds according to the present invention means that in humans it triggers an odor sensation which is preferably pleasant; it is therefore conventionally used for perfuming industrial and sanitary articles, washing agents, cleaning agents, personal hygiene products, cosmetics and the like. For the purposes of the present invention and appended claims, the term "odorant" includes "aroma substances". Aroma substances is the term usually used to designate substances which provide odor and/or flavor to foodstuffs.

The compounds of formula (I) may be used alone, as mixtures thereof, or in combination with a base material.

As used herein, the "base material" includes all known fragrance/flavor materials selected from the extensive range of natural products like: essential oils, extracts, resinoids or isolates and synthetic materials currently available, such as: hydrocarbons, alcohols, aldehydes and ketones, ethers and acetals, esters and lactones, nitriles, oximes or heterocycles, and/or in admixture with one or more ingredients or excipients/adjuvants conventionally used in conjunction with odorants in fragrance and/or flavor compositions, for example: solvents/diluents, stabilizers, carrier materials, and other auxiliary agents commonly used in the art.

The compounds according to formula (I) may be used in a broad range of fragrance applications, e.g. in any field of fine and functional perfumery, such as perfumes, air care products, household products, laundry products, body care products and cosmetics. The compounds can be employed in widely varying amounts, depending upon the specific application and on the nature and quantity of other odorant ingredients.

According to a preferred embodiment of the invention, the fragrance, flavor and/or deodorizing/masking composition according to the present invention contains at least one compound according to formula (I) as previously described, in quantities between 0.0001 and 95 wt. (N), for example between 0.001 and 25 wt. %, preferably between 0.01 and 15 wt. %, more advantageously between 0.1 and 10 wt. %, in particular between 1 and 5 wt. %, in each case relative to the entire composition.

According to a particularly preferred embodiment of the invention, in addition to the compound of formula (I) according to the present invention, the fragrance, flavor and/or deodorizing/masking composition according to the present invention contains additional odorants, for example in a quantity of 0.1 to 99.9 wt. %, preferably 5-90 wt. %, in particular 15-70 wt. %, relative to the entire fragrance and/or flavor composition.

The compounds of formula (I) as described hereinabove may be employed in a consumer product base simply by directly mixing at least one compound of formula (I), or a fragrance composition comprising said compound of formula (I) with the consumer product base; or they may, in an earlier step, be entrapped with an entrapment material, for example, polymers, capsules, microcapsules and/or nanocapsules, liposomes, film formers, absorbents such as active carbon or zeolites, cyclic oligosaccharides and mixtures of two or more thereof, or they may be chemically bonded to substrates, which are adapted to release the fragrance molecule upon application of an external stimulus such as light, high temperature, enzyme, air, water or the like, and then mixed with the consumer product base.

Thus, the invention can be useful for existing methods of manufacturing a fragrance, flavor and/or deodorizing/masking composition, comprising the incorporation of a compound of formula (I), as a fragrance, flavor and/or deodorizing/making ingredient, either by directly admixing the compound to the consumer product base or by admixing a fragrance, flavor and/or deodorizing/masking composition comprising said compound of formula (I), which may then be mixed with a consumer product base, using conventional techniques and methods. Through the addition of an olfactory-acceptable amount of at least one compound of formula (I) of the present invention as hereinabove described, the odor notes of a consumer product base can be improved, enhanced, and/or modified.

The present invention provides fragrance, flavor and/or deodorizing/masking compositions comprising a compound of formula (I)

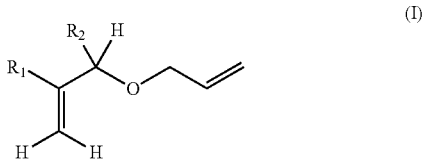

(I)

wherein $R_1$ is either an alkyl group having up to 9 carbon atoms or an alkenyl group having up to 9 carbon atoms and $R_2$ is hydrogen or an alkyl or alkenyl group having up to 5 carbon atoms; in an embodiment when R2 is hydrogen, R1 can't be tert-butyl; in an embodiment, when R2 is hydrogen, R1 can't be pentyl.

In an embodiment according to the present invention, the fragrance, flavor and/or deodorizing/masking composition comprises the compound of formula (I) which is selected from 2-((allyloxy)methyl)hex-1-ene, 2-((allyloxy)methyl)-3-methylbut-1-ene, 2-(allyloxy)-4-methyl-3-methylenepentane, 4-(allyloxy)-2-methyl-3-methylenehexane, 2-((allyloxy)methyl)hept-1-ene, 2-((allyloxy)methyl)oct-1-ene, 2-((allyloxy)methyl)undec-1-ene, 2-((allyloxy)methyl)-3,7-dimethylocta-1,6-diene, and/or a mixture of two or more of the said compounds of formula (I).

In an embodiment, the present invention also claims novel compounds of formula (I) useful in a fragrance, flavor and/or deodorizing/masking composition.

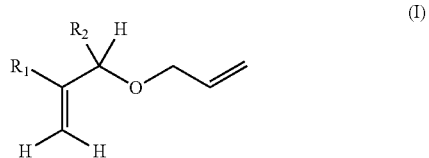

(I)

wherein $R_1$ is either an alkyl group having up to 9 carbon atoms or an alkenyl group having up to 9 carbon atoms and $R_2$ is hydrogen or an alkyl or alkenyl group having up to 5 carbon atoms, with the proviso that
when R2 is hydrogen, R1 can't be tert-butyl, and
when R2 is hydrogen, R1 can't be pentyl.

In an embodiment, the compound of formula (I) useful in a fragrance, flavor and/or deodorizing/masking composition is selected from 2-((allyloxy)methyl)hex-1-ene, 2-((allyloxy)methyl)-3-methylbut-1-ene, 2-(allyloxy)-4-methyl-3-methylenepentane, 4-(allyloxy)-2-methyl-3-methylenehexane, 2-((allyloxy)methyl)oct-1-ene, 2-((allyloxy)methyl)undec-1-ene, 2-((allyloxy)methyl)-3,7-dimethylocta-1,6-diene, and/or a mixture of two or more of the said compounds.

The Applicants have also discovered that, from an olfactory perspective, the compounds of formula (I) have a distinctly green, fruity, pear and/or waxy profile that lends itself directly to use in fruity compositions such as for example pear, quince, kiwi, and/or pineapple. Indeed, the compounds of formula (I) exhibit more waxy characteristics, reminiscent of the entire natural fruit. It is also more versatile, with easily recognizable applications toward related fruits (quince/apple) as well as unrelated fruits (kiwi/pineapple). Furthermore, compared to other odorants like e.g. Pear Ester, the compounds of formula (I) have greater depth and presence together with an additional property which makes it very valuable, i.e. their greater stability in various application media in particular basic media. For example, when $R_1$ is selected as an alkyl group having 4 carbon atoms, the Applicants have discovered that a very diffusive, green, fruity, and pear oriented olfactive note could be obtained.

The compounds of formula (I) can advantageously be prepared from corresponding 2- and/or 1-substituted allyl alcohols of formula (II)

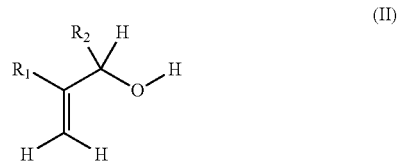

(II)

wherein $R_1$ is either an alkyl group having up to 9 carbon atoms or an alkenyl group having up to 9 carbon atoms and $R_2$ is hydrogen or an alkyl or alkenyl group having up to 5 carbon atoms by using a Williamson ether synthesis step, for example by reacting the alcohols of the formula (II) with an allyl bromide and/or an allyl chloride in presence of a base such as sodium hydride and/or sodium hydroxide and/or potassium hydroxide. The resulting ethers are then preferably purified by distillation.

In said alcohols compounds of formula (II), $R_1$ is either an alkyl group having up to 9 carbon atoms or an alkenyl group having up to 9 carbon atoms and $R_2$ is hydrogen or and alkyl or alkenyl group having up to 5 carbon atoms; both $R_1$ and $R_2$ can be straight chain and/or branched alkyls.

In an embodiment according to the present invention, the alcohols as defined in formula (II) can advantageously be synthesized from 2-substituted acroleins of formula (III)

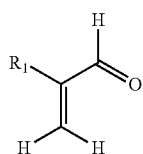
(III)

wherein $R_1$ is either an alkyl group having up to 9 carbon atoms or an alkenyl group having up to 9 carbon atoms, either by reduction, for example with sodium borohydride or lithium aluminum hydride or by nucleophilic addition of organometallic reagent, for example an appropriate alkyl magnesium halide, $R_2MgX$ e.g. MeMgCl In an embodiment according to the present invention, the acroleins of formula (III) can advantageously be synthesized via a reaction of an aldehyde of formula (IV) with formaldehyde (or a formaldehyde source)

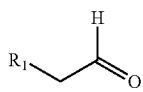
(IV)

wherein $R_1$ is either an alkyl group having up to 9 carbon atoms (straight chain and/or branched alkyl) or an alkenyl group having up to 9 carbon atoms, for example by using formaldehyde (e.g. 37% aqueous formaldehyde) or formaldehyde source (e.g. paraformaldehyde) and boric acid and secondary amine combination, for example the combination of boric acid and secondary amine such as diethanolamine; in an embodiment of the present invention, an acid base combination of 4-methoxybenzoic acid and di-n-butyl amine could also be used for the reaction of aldehydes with formaldehyde.

The above reaction of aldehydes with formaldehyde results in formation of 2-substituted acroleins of formula (III) as defined above.

In an embodiment according to the present invention, the compounds of formula (I) can advantageously be prepared by the three following consecutive steps:

Subjecting an aldehyde of formula (IV)

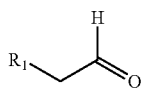
(IV)

wherein $R_1$ is either an alkyl group having up to 9 carbon atoms or an alkenyl group having up to 9 carbon atoms, to a reaction with formaldehyde to form 2-substituted acroleins of formula (III)

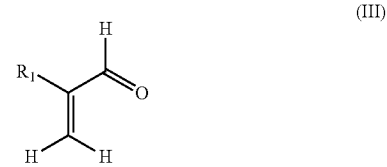
(III)

wherein $R_1$ is either an alkyl group having up to 9 carbon atoms or an alkenyl group having up to 9 carbon atoms, Subjecting the 2-substituted acroleins of formula (III) of the previous step to a reduction or nucleophilic addition of organometallic reagent reaction step to form 1-substituted allyl alcohols of the formula (II)

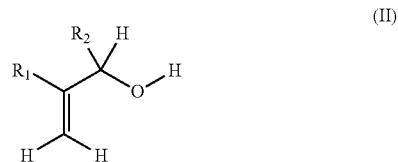
(II)

wherein $R_1$ is either an alkyl group having up to 9 carbon atoms or an alkenyl group having up to 9 carbon atoms and $R_2$ is hydrogen or an alkyl or alkenyl group having up to 5 carbon atoms, and Subjecting the 1-substituted allyl alcohols of formula (II) of the previous step to a Williamson ether synthesis step to form the compounds of formula (I)

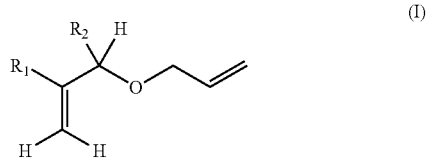
(I)

wherein $R_1$ is either an alkyl group having up to 9 carbon atoms or an alkenyl group having up to 9 carbon atoms and $R_2$ is hydrogen or an alkyl or alkenyl group having up to 5 carbon atoms.

An illustrative scheme of the synthesis of the compounds of formula (I) according to the present invention is represented below

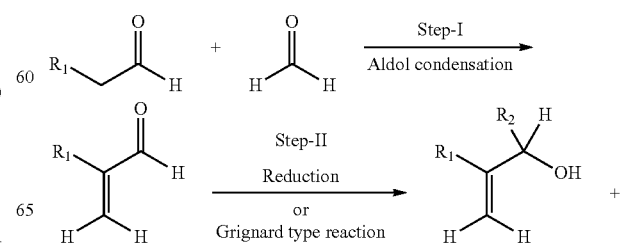

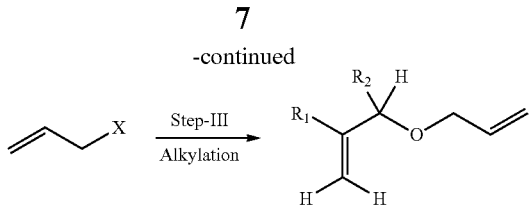

wherein aldehydes with two hydrogens in alpha position are converted into acroleins by reaction with formaldehyde (in form of paraformaldehyde or formalin); acroleins are reduced with sodium borohydride to the corresponding allyl alcohols; allyl alcohols are subjected to Williamson synthesis using for instance allyl chloride to form the bis allyl ethers.

In an embodiment of the present invention, the aldol condensation, in particular the reaction of aldehydes with formaldehyde (first preparation step) is performed in the presence of a catalyst based on boric acid and a secondary amine, preferably diethanolamine. By developing this specific preparation step, the Applicants have significantly improved the overall preparation process thanks to low odor impact of the catalyst, e.g. when compared to other catalytic systems for aldol condensation which use strongly smelling amines like diethylamine, dibutyl amine, piperidine or pyrrolidine or unpleasantly smelling acids like fatty acids and low catalyst load when comparing to similar catalytic system like for instance dibuthyl amine/hexanoic acid or piperidine/stearic acid. Combination of availability, low cost of the components of the said catalytic system, and relatively low molecular mass of boric acid compared to other acids with similar pKa is particularly advantageous as it positively influences economic aspect of the methylenation process using the said catalytic system.

In an embodiment of the present invention there is also provided a process for reacting an aldehyde of formula (IV)-(a)

(IV)-a wherein $R_1$ is an alkyl group having up to 9 carbon atoms, an alkenyl group having up to 9 carbon atoms, an alkynyl group having up to 9 carbon atoms, a phenyl group, a substituted aryl group having up to 9 carbon atoms, an oxo-alkyl group having up to 9 carbon atoms, an alkoxyaryl group containing up to 9 carbon atoms or a (substituted) benzyl group having up to 9 carbon atoms, with formaldehyde or a formaldehyde source to form 2-substituted acroleins of formula (III)-(a)

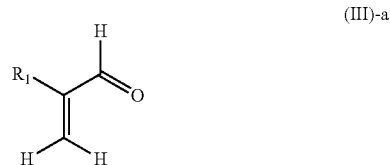

(III)-a wherein $R_1$ is an alkyl group having up to 9 carbon atoms, an alkenyl group having up to 9 carbon atoms, an alkynyl group having up to 9 carbon atoms, a phenyl group, a substituted aryl group having up to 9 carbon atoms, an oxo-alkyl group having up to 9 carbon atoms, an alkoxyaryl group containing up to 9 carbon atoms or a (substituted) benzyl group having up to 9 carbon atoms.

In an embodiment of the present invention, the alkyl, alkenyl, alkynyl and oxo-alkyl groups of the aldehyde of formula (IV)-(a) can be linear, branched or cyclic. In an embodiment according to the present invention, $R_1$ of the aldehyde of formula (IV)-(a) can be ethyl, n-propyl, i-propyl, n-butyl, s-butyl, t-butyl, i-butyl, 1-pentyl, 2-pentyl, 3-pentyl, 1-hexyl, 2-hexyl, 3-hexyl, 1-heptyl, 2-heptyl, 3-heptyl, 4-heptyl, 1-octyl, 2-octyl, 3-octyl, 4-octyl, 1-nonyl, 2-nonyl, 3-nonyl, 4-nonyl, 5-nonyl, cyclopropyl, cyclobutyl, cyclopentyl, cyclohexyl, 1-(cyclohexylmethyl), (methoxy)methyl, (ethoxy)methyl, vinyl, 1-propenyl, 1-isobutenyl, 3-butenyl, 5-(2-methylpent-2-en)yl, 4-penten-2-enyl, 4-pent-1-enyl, 4-(4-methylpent-1-en)yl, 5-(2,5-dimethylhex-2-en)yl, 2,2,3-trimethylcyclopent-3-en-1-yl, benzyl, phenyl, or 4-methoxyphenyl.

In an embodiment of the present invention, the alkyl, alkenyl, alkynyl and oxo-alkyl groups of the 2-substituted acroleins of formula (III)-(a) can be linear, branched or cyclic. In an embodiment according to the present invention, $R_1$ of the 2-substituted acroleins of formula (III)-(a) is ethyl, n-propyl, i-propyl, n-butyl, s-butyl, t-butyl, i-butyl, 1-pentyl, 2-pentyl, 3-pentyl, 1-hexyl, 2-hexyl, 3-hexyl, 1-heptyl, 2-heptyl, 3-heptyl, 4-heptyl, 1-octyl, 2-octyl, 3-octyl, 4-octyl, 1-nonyl, 2-nonyl, 3-nonyl, 4-nonyl, 5-nonyl, cyclopropyl, cyclobutyl, cyclopentyl, cyclohexyl, 1-(cyclohexylmethyl), (methoxy)methyl, (ethoxy)methyl, vinyl, 1-propenyl, 1-isobutenyl, 3-butenyl, 5-(2-methylpent-2-en)yl, 4-penten-2-enyl, 4-pent-1-enyl, 4-(4-methylpent-1-en)yl, 5-(2,5-dimethylhex-2-en)yl, 2,2,3-trimethylcyclopent-3-en-1-yl, benzyl, phenyl, or 4-methoxyphenyl.

The process is characterised in that this reaction (Step I) is performed in the presence of boric acid and a secondary amine (e. g. dibutylamine, preferably diethanolamine). In an embodiment according to the present invention the synthesis of acroleins of the formula (III)-(a) (for example those of formula (III)), that is the reaction of aldehydes with formaldehyde (Step I), can advantageously be performed by reacting aldehyde of formula (IV)-(a) (for example those of formula (IV)) with aqueous formaldehyde (or an alternative source of formaldehyde, e.g. paraformaldehyde) in the presence of a dialkylamine and boric acid when the molar ratio of dialkylamine to the intermediate aldehyde of formula (IV)-(a) is between 0.01 and 99.9, for example between 0.02 and 0.2; and/or the molar ratio of boric acid to the intermediate aldehyde of formula (IV)-(a) is between 0.01 and 99.9, for example between 0.02 and 0.2.

In an embodiment according to the present invention the synthesis of acroleins of the formula (III)-(a) (Step I) is preferentially performed without addition of additional solvents, however any suitable polar on non-polar, protic or non-protic solvent can be used.

In an embodiment according of the present invention the synthesis of acroleins of the formula (III)-(a) is performed between 20 and 95° C., more preferably between 60 and 80° C.

In an embodiment of the present invention, the claimed fragrance, flavor and/or deodorizing/masking composition is advantageously used as a perfumery composition. Perfumery compositions according to the present invention generally include a perfume, a cologne, an eau du toilette, and/or an eau de parfum. In an embodiment of the present invention, the claimed fragrance, flavor and/or deodorizing/masking composition is advantageously used in a cosmetic formulation, a personal care product, a cleansing product, a fabric softener, and/or air freshener, and the like. Furthermore, it is within the purview of embodiments of the invention that the novel fragrance, flavor and/or deodorizing/masking composition(s) and/or novel compound(s) of formula (I) described herein may be integrated into building materials, wall and floor coverings, vehicle components, and the like.

In general, in addition to the novel odorant and/or fragrance, flavor and/or deodorizing/masking compositions described herein, suitable fragrance, flavor or deodorizing compositions may advantageously include conventional ingredients such as, for example, solvents, carriers, stabilizers, emulsifiers, moisturizers, dispersants, diluents, thickeners, thinners, other odorants, and/or adjuvants, and the like.

The compounds of formula (I) combine with numerous known natural or synthetic fragrance, flavor and/or deodorizing/masking materials, whereby the range of the natural ingredients can embrace not only readily-volatile but also semi-volatile and slightly-volatile components and the range of the synthetic ingredients can embrace representatives from many classes of substances, such as described in Steffen Arctander, Perfume and Flavor Chemicals, vol. 1&2, Montclair, N.J., 1969; Steffen Arctander, Perfume and Flavor Materials of Natural Origin, Elizabeth, N.J., 1960 or Horst Surburg, Johannes Panten, Common Fragrance and Flavor Materials, Wiley-VCH, Weinheim, 2016 and as will be evident from the following nonlimitting compilation:

Natural Products Such as:

Ajowan oil, Amyris oil, Armoise oil, Artemisia oil, Basil oil, Bees wax absolute, Bergamot oil, Birch tar oil, Black pepper oil, Black pepper oleoresin, Camphor oil, Cananga oil, Caraway oil, Cardamom oil, Carrot seed oil, Castoreum absolute, Cedar leaf oil, Cedarwood oil, Celery seed oil, Chamomile oil, Cinnamon bark oil, Cinnamon leaf oil, Cistus absolute, Cistus oil, Citronella oil, Citronella terpenes, Clary sage oil, Clove oil rectified, Cognac oil white, Coriander seed oil, Cumin seed oil, Cypress oil, Davana oil, Dill seed oil, Elemi oil, Elemi resinoid, Eucalyptus oil, Fir needle oil, Galbanum oil, Geranium oil, Ginger oil Indian, Grapefruit oil, Guaiacwood oil, Gurjun balsam, Jasmin absolute, Jatamansi oil, Juniper berry oil, Juniper leaf oil, Kachur oil, Labdanum absolute, Labdanum resinoid, Lavender oil, Lemon oil, Lemon oil terpenes, Lemongrass oil, Lime oil, Litsea cubeba oil, Litsea cubeba terpenes, Lobhan choya resinoid, Mandarin oil, Mentha arvenis oil, Mentha citrata oil, Mimosa absolute, Myrrh resinoid, Nagarmotha oil, Nutmeg oil, Oakmoss absolute, Oakmoss resinoid, Olibanum oil, Olibanum resinoid, Orange oil, Origanum oil, Palma rosa oil, Patchouli oil, Peppermint oil, Peru Balsam resinoid, Petitgrain oil, Pine needle oil, Pink pepper oil, Rose absolut, Rose oil, Rosemary oil, Sandalwood oil, Seaweed absolute, Spearmint oil, Sugandh kokila oil, Sugandh mantri oil, Tagete oil, Tolu Balsam resinoid, Tuberose absolute, Turmeric oil, Turpentine oil, Valerian oil, Vetiver oil, Vetiver terpenes.

Synthetic Raw Materials for Instance:

Esters such as: Aldehyde C16, Allyl amyl glycolate, Allyl caproate, Allyl cyclohexyl propionate, Allyl heptoate, Allyl phenoxy acetate, Amyl acetate iso, Amyl benzoate, Amyl butyrate, Amyl caproate, Amyl cinnamate, Amyl isovalerate, Amyl phenyl acetate, Amyl propionate, Amyl salicylate iso, Amyris acetate, Anisyl acetate, Benzyl acetate, Benzyl benzoate, Benzyl butyrate, Benzyl cinnamate, Benzyl formate, Benzyl isobutyrate, Benzyl isoeugenol, Benzyl propionate, Benzyl salicylate, Benzyl tiglate, Butyl acetate, Butyl butyrate, Butyl butyryl lactate, Caryophyllene acetate, Cedryl acetate, Cinnamyl acetate, Cinnamyl butyrate, Cis-3-hexenyl acetate, Cis-3-hexenyl benzoate, Cis-3-hexenyl caproate, Cis-3-hexenyl formate, Cis-3-hexenyl isobutyrate, Cis-3-hexenyl-2-methyl butyrate, Cis-3-hexenyl propionate, Cis-3-hexenyl salicylate, Cis-3-hexenyl tiglate, Citronellyl acetate, Citronellyl butyrate, Citronellyl formate, Citronellyl isobutyrate, Citronellyl propionate, Citronellyl tiglate, Cyclabute, Cyclogalbanate, Cyclohexyl ethyl acetate, Decyl acetate, Dibutyl phthalate, Diethyl malonate, Diethyl phthalate, Dihydromyrcenyl acetate, Dimethyl octanyl acetate, Dimethyl phenyl ethyl carbinyl acetate, Dioctyl adipate, Dioctyl phthalate, Dimethyl benzyl carbinyl acetate, Dimethyl benzyl carbinyl butyrate, Ethyl linalyl acetate, Ethyl 2-methyl butyrate, Ethyl 3-phenyl propionate, Ethyl acetate, Ethyl acetoacetate, Ethyl benzoate, Ethyl butyrate, Ethyl caprate, Ethyl caproate, Ethyl caprylate, Ethyl cinnamate, Ethyl heptoate, Ethyl hexyl acetate, Ethyl isobutyrate, Ethyl laurate, Ethyl pelargonate, Ethyl phenoxy acetate, Ethyl phenyl acetate, Ethyl phenyl glycidate, Ethyl propionate, Ethyl safranate, Ethyl salicylate, Ethyl valerate, Eugenyl acetate, Evernyl, Fenchyl acetate, Floramat, Frescolat ML, Fructone, Fruitate, Geranyl acetate, Geranyl butyrate, Geranyl formate, Geranyl propionate, Geranyl tiglate, Givescone, Guaiol acetate, Hedionate, Hedione, Helvetolide, Herbanate, Hexyl acetate, Hexyl benzoate, n-Hexyl butyrate, Hexyl caproate, Hexyl isobutyrate, Hexyl propionate, Hexyl salicylate, Isobornyl acetate, Isobutyl acetate, Isobutyl phenyl acetate, Isobutyl salicylate, Isoeugenyl acetate, Isononyl acetate, Isopentyrate, Isopropyl 2-methyl butyrate, Isopropyl myristate, Jasmonyl, Liffarome, Linalyl acetate, Mahagonate, Manzanate, Menthanyl acetate, Menthyl acetate, Methyl benzoate, 2-Methyl butyl acetate, Methyl camomille, Methyl cinnamate, Methyl cyclogeranate, Methyl heptine carbonate, Methyl laurate, Methyl octine carbonate, Methyl phenyl acetate, Methyl salicylate, Methyl-2-methyl butyrate, Neofolione, Nopyl acetate, Octenyl acetate, Octyl acetate, Octyl isobutyrate, Para cresyl acetate, Para cresyl isobutyrate, Para cresyl phenyl acetate, Pear ester, Peranat, Phenoxy ethyl isobutyrate, Phenyl ethyl acetate, Phenyl ethyl butyrate, Phenyl ethyl formate, Phenyl ethyl isobutyrate, Phenyl ethyl phenyl acetate, Phenyl ethyl propionate, Phenyl ethyl salicylate, Phenyl ethyl tiglate, Phenyl propyl isobutyrate, Prenyl acetate, Romandolide, Sagecete, Styrallyl acetate, Styrallyl propionate, Tangerinol, Terpinyl acetate, Thesaron, Trans-2-hexenyl acetate, Tropicate, Verdox, Verdyl acetate, Verdyl propionate, Vertenex, Vetikol acetate, Vetiveryl acetate, Yasmolys.

Lactones such as: Ambrettolide, Arova N, Celeriax, Decalactone delta, Decalactone gamma, Dodecalactone delta, Dodecalactone gamma, Ethylene brassylate, Exaltolide, Heptalactone gamma, Hexalactone delta, Hexalactone gamma, Methyl laitone, Methyl octalactone, Nonalactone delta, Nonalactone gamma, Octahydrocoumarine, Octalactone delta, Octalactone gamma, Rootylone, Silvanone supra, Undecalactone delta, Undecalactone gamma, Valerolactone gamma, 10-OxaHexaDecanolide (OHD musk), Coumarin, Habanolide, Jasmolactone.

Aldehydes such as: Acetaldehyde, Adoxal, Aldehyde C10, Aldehyde C11 iso, Aldehyde C11 moa, Aldehyde C11 undecylenic, Aldehyde C11 undecylic, Aldehyde C12 lauric, Aldehyde C12 MNA, Anisaldehyde, Amyl cinnamaldehyde, Benzaldehyde, Bourgeonal, Campholenaldehyde, Cantonal, Cetonal, Cinnamic aldehyde, Cis-4-decenal, Cis-6-nonenal, Citral, Citronellal, Citronellyl oxyacetaldehyde, Cocal, Cuminaldehyde, Curgix, Cyclal C, Cyclamen aldehyde, Cyclomyral, Cyclovertal, Decenal 9, Dupical, Empetal, Ethyl vanillin, Floralozone, Florhydral, Geraldehyde, Helional, Heliotropin, Heptanal, Hexanal, Hexyl cinnamaldehyde, Hivernal neo, Hydratropaldehyde, Hydroxycitronellal, Intreleven aldehyde, Isobutavan, Isocyclocitral, Isovaleraldehyde, Lilial, Limonenal, Maceal, Mefranal, Melonal, Methyl cinnamaldehyde, Nonadien-al trans-2 cis-6, Nonanal, Octanal, Oncidal, Para tolyl aldehyde, Phenyl acetaldehyde, Phenyl propyl aldehyde, Precyclemone B, Safranal, Salicylaldehyde, Scentenal, Syringa aldehyde, Trans-4-decenal, Trans-2-dodecenal, Trans-2-hexenal, Trans-2-nonenal, Trifernal, Vanillin, Veratraldehyde, Vernaldehyde Ketones such as: Acetanisol, Acetoin, Acetophenone, Aldron, Allyl ionone, Benzophenone, Benzyl acetone, Calone, Camphor, Carvone d-, Carvone l-, Cashmeran, Cedryl methyl ketone, Cepionate, Claritone, Cosmone, Crysolide, Cyclotene, Damascenone, Damascone alpha, Damascone beta, Damascone delta, Damascone gamma, Diacetyl, Dihydro beta ionone, Dihydro isojasmonate, Dimethyl octenone, Dynascone, Ethyl amyl ketone, Ethyl maltol, Fenchone, Filbertone, Geranyl acetone, Globanone, Heptyl cyclopentanone, Ionone alpha, Ionone beta, Ionone pure, Iriswood, Irone alpha, Iso E Super, Isofenchone, Isojasmone T, Isolone K, Isomenthone, Isophorone, Jasmone cis-, Kambernoir, Kephalis, Koavone, Lavendinal, Maltol, Menthone, Methyl acetophenone, Methyl amyl ketone, Methyl heptenone, Methyl hexyl ketone, Methyl ionone gamma, Methyl naphthyl ketone beta, Methyl nonyl ketone, Muscenone, Muscone, Nectaryl, Orinox, OTBC Ketone, Para tertbutylcyclohexanone, Patchwood, Phantolid, Pharaone, Piperitone, Plicatone, Raspberry ketone, Raspberry ketone methyl ether, Safraleine, Spirogalbanone pure, Tonalid, Trimofix O, Veloutone, Vetikon.

Alcoholos such as: Alcohol oxo C13, Amber core, Ambermax, Ambrinol, Amyl vinyl carbinol, Anisic alcohol, Bacdanol, Benzyl alcohol, Butanol, Cedrol crystals, Cinnamic alcohol, Citronellol, Coranol, Decanol, Dimethyl benzyl carbinol, Dimethyl octanol, Dimethyl phenyl ethyl carbinol, Dimetol, Fenchol, Hexanol, Isoborneol, Isobornyl cyclohexanol, Javanol, Keflorol, Kohinool, Lauryl alcohol, Lilyflore, Linalool oxide, Mayol, Menthol, Norlimbanol, Octanol, Osyrol, Para tertbutylcyclohexanol, Phenoxanol, Phenoxyethanol, Phenyl ethyl alcohol, Phenyl propyl alcohol, Propylene glycol, Rosaphen, Rose glycol, Styrallyl alcohol, Tricyclodecane dimethanol, Tetrahydro linalool, Tetrahydro myrcenol, Timberol, Undecavertol, Cis-3-hexenol, Citronellol laevo, Cyclofloranol, Dihydrolinalool, Dihydromyrcenol, Dimyrcetol, Ebanol, Geraniol, Isopulegol, Linalool, Nerol, Nerolidol, Nonadien-ol trans-2 cis-6, Polysantol, Rosalva, Sandalmysore core, Sandalore, Terpinen-4-ol, Terpineol, Trans-2-hexenol Phenols such as: Butylated hydroxyanisole, Dihydroeugenol, Dimethyl hydroquinone, Dimethyl resorcinol, Eugenol pure, Guaiacol, Isoeugenol, Meta cresol, Methyl diantilis, Para cresol, Propenyl guaethol, Thymol, Ultravanil.

Ethers such as: Ambroxan, Anethole, Anther, Benzyl isoamyl ether, Benzyl isopropyl ether, Benzyl isovalerate, Boisiris, Cedramber, Cetalox, Decyl methyl ether, Dibenzyl ether, Dihydro rose oxide, Diphenyl oxide, Doremox, Estragole, Ethyl linalool, Eucalyptol, Galaxolide, Gyrane, Herbavert, Lime oxide, Madrox, Methyl isoeugenol, Naphthyl isobutyl ether beta, Nerol oxide, Nerolin bromelia, Para cresyl butyl ether, Para cresyl methyl ether, Petiole, Phenyl ethyl methyl ether, Rhubafuran, Rose oxide, Rosyrane, Trisamber, Vetylbois K, Yara yara Acetals such as: Acetal CD, Acetal R, Amberketal, Boisambrene forte, Citrathal, 1,1-Diethoxyethane, Emeraldine, Freshopal, Herboxane, Indoflor, Jacinthaflor, Magnolan, Spirambrene, Viridine, Elintaal, Glycolierral, Karanal, Methyl pamplemousse, Hydrocarbons such as: Bisabolene, Camphene, Carene delta 3, Caryophyllene, Cedrene, Cymene para, Dipentene, Diphenyl methane, Isolongifolene, Limonene d-, Longifolene, Myrcene, Naphthalene, Ocimene, Pinene alpha, Pinene beta, Styrene, Terpinene gamma, Terpinolene, 1,3,5-Undecatriene, Verdoracine.

Sulphur compounds such as: Corps cassis, Dibutyl sulphide, Dimethyl sulphide, Exovert, Grapefruit thiol, Oxane, Ribes mercaptan, Sulfurol, Thiocineol.

Nitriles such as: Cinnamyl nitrile, Citronellyl nitrile, Citronitrile, Clonal, Cumin nitrile, Hexyl cyclopentanone, Irisnitrile, Lemonile, Peonile, Tridecyl nitrile, Agrumen nitrile, n-decyl nitrile.

Oximes such as: Buccoxime, Labienoxime, Stemone.

Nitrogen heterocycles such as: 2-acetylpyrazine, 2-acetylpyridine, sec-butylquinoline, Corps racine, 2-ethyl-3,5 (or 6)-dimethylpyrazine, Furfuryl pyrrole, Indole, Isobutyl quinoline, 2-Isobutyl-3 (or 6)-methoxypyrazine, Isopropyl quinoline, Maritima, p-methyl quinoline, Skatol, 2,3,5-trimethylpyrazine.

Nitro compound such as: Musk Ketone

Schiff bases such as: Aurantiol, Helianthral, Ligantraal, Verdantiol.

Other materials such as: Acetanilide, Gardamide, Paradisamide, Dimethyl anthranilate, Methyl anthranilate, n-Butyric acid, Capric acid, Caproic acid, Caprylic acid, Phenylacetic acid, Caryophyllene oxide, Cedroxyde, Tobacarol The compounds of formula (I) can accordingly be used for the production of compositions and, as will be evident from the foregoing compilation, a wide range of known odorants/fragrance, flavor and/or deodorizing/masking materials. In the production of such compositions, the known fragrance, flavor and/or deodorizing/masking materials referred to earlier can be used according to methods which are known to the perfumer such as, for example, according to W. A. Poucher, Perfumes, Cosmetics and Soaps 2, 7th Edition, Chapman and Hall, London 1974.

In an embodiment of the present invention, the claimed fragrance, flavor and/or deodorizing/masking composition comprises in addition to the allyl ethers at least one ester and/or one alcohol, preferably at least a mixture of ester and alcohol; the said ester and/or alcohol are preferably selected from the list defined herein above. In an embodiment of the present invention, the claimed odorant composition is characterised by a total content of the compound(s) of formula (I) together with the ester(s) and/or alcohol(s) which is superior to 25 wt %, preferably superior to 50 wt %, for example superior to 75 wt %, or even superior to 90 wt %.

In another embodiment of the present invention, the claimed fragrance, flavor and/or deodorizing/masking composition comprises in addition to the allyl ethers their respective parent alcohol of general formula (II). In an embodiment of the present invention, the claimed odorant composition is characterized by a total content of the allyl ethers of general formula (I) together with their respective parent alcohol of formula (II) which is superior to 5 wt %, e.g. superior to 25 wt %, preferably superior to 50 wt %, for example superior to 75 wt %, or even superior to 90 wt %.

The disclosure is further illustrated by the following examples which in no way should be construed as being further limiting. One skilled in the art will readily appreciate that the specific methods and results described are merely illustrative.

All stereoisomers of the compounds of the instant disclosure are contemplated, either in admixture or in pure or substantially pure form. The compounds of the present disclosure can have asymmetric centers at any of the carbon atoms, consequently, claimed compounds can exist in enantiomeric, or diastereomeric forms, or in mixtures thereof. The processes for preparation can utilize racemates, (pure) enantiomers, nonracemic mixtures of enantiomers, diastereomers or mixtures of diasteremers as starting materials. When diastereomeric or enantiomeric products are obtained as mixtures, they can be separated by conventional methods for example, chromatographic separation or fractional crystallization or through diastereomeric salt formation. When intended, a desired enantiomer or diastereomer can also be obtained by following appropriate enantioselective or diastereoselective reactions.

EXAMPLES

Example 1

Synthesis of 2-((allyloxy)methyl)hex-1-ene

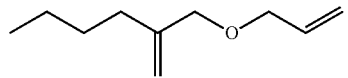

Step-1: Synthesis of 2-methylenehexanal:

Hexanal (3.88 kg, 38.7 mol, 1 eq.) was added to a mixture of aqueous 37% formaldehyde (3.78 kg, 46.5 mol, 1.2 eq.), di-n-butylamine (252 g, 1.95 mol, 0.05 eq.) and p-anisic acid (295 g, 1.94 mol, 0.05 eq.) at 10-15° C. over a period of 2 h while stirring. After completion of addition, the reaction mixture was stirred for 2 h at 50° C. Subsequently, the reaction mixture was cooled to 25° C., organic phase was separated, washed with water (3×2 L) and dried over sodium sulfate (250 g). The crude product was distilled in vacuo (45-49° C./53 mbar) to afford 2-methylenehexanal (3.98 kg, 91%) as a colorless liquid.

$^1$H NMR (400 MHz, CDCl$_3$): δ 0.91 (t, J=7.2 Hz, 3H), 1.30-1.47 (m, 4H), 2.03-2.07 (m, 2H), 4.85-4.86 (m, 1H), 5.00 (m, 1H), 10.05 (s, 1H).

$^{13}$C NMR (100 MHz, CDCl$_3$): δ 13.6, 22.0, 27.3, 29.9, 133.7, 150.5, 194.5.

Step-2: Synthesis of 2-methylenehexan-1-ol:

Sodium borohydride (383 g, 10.1 mol, 272 meq.) was added to a mixture of 2-methylenehexanal (4.18 kg, 37.3 mol, 1 eq.) and water (5.60 L) at 10-15° C. over a period of 4 h while stirring. Then the reaction mixture was stirred for 3 h at 25° C. Subsequently, the reaction mixture was quenched with aqueous 10% hydrogen chloride (3 L). The organic phase was separated and was successively washed with water (1×3 L), aqueous 10% sodium carbonate (1×3 L) and brine (1×3 L). The organic phase (4.13 kg) was distilled in vacuo (52-54° C./4 mbar) to afford 2-methylenehexan-1-ol (3.94 kg, 92%) as a colorless liquid.

$^1$H NMR (400 MHz, CDCl$_3$): δ 0.91 (t, J=7.2 Hz, 3H), 1.30-1.47 (m, 4H), 2.03-2.07 (m, 3H), 4.05 (s, 2H), 4.85-4.86 (m, 1H), 5.00 (m, 1H).

$^{13}$C NMR (100 MHz, CDCl$_3$): δ 13.8, 22.6, 32.8, 35.6, 65.4, 108.6, 149.0.

Step-3: Synthesis of 2-(allyloxy)methyl)hex-1-ene:

Powdered potassium hydroxide (1.76 kg, 31.4 mol, 1.99 eq.) was added to a mixture of 2-methylenehexan-1-ol (1.80 kg, 15.8 mol, 1 eq.) and tetra-n-butyl ammonium bromide (255 g, 791 mmol, 0.05 eq.) at 25° C. over a period of 2 h. Then allyl chloride (3.01 kg, 39.3 mol) was added at 10-15° C. over a period of 6 h while stirring. The reaction mixture was stirred at 25° C. for 16 h. Subsequently, the reaction mixture was filtered through a Buchner funnel and the solid was washed with methyl tert-butyl ether (1 L). The filtrate was successively washed with water (2 L), aqueous 5% hydrogen chloride (300 mL), aqueous 5% sodium carbonate (1 L) and brine (2 L). The volatiles were removed under reduced pressure (45° C./133 mbar). The residue (2.46 kg) was distilled in vacuo (34-36° C./3 mbar) to afford 2-((allyloxy)methyl)hex-1-ene (1.91 kg, 78%) as a colorless liquid. GC purity 97.5%.

$^1$H NMR (400 MHz, CDCl$_3$): δ 0.91 (t, J=7.2 Hz, 3H), 1.31-1.47 (m, 4H), 2.03-2.07 (m, 2H), 3.91-3.94 (s, 2H), 3.94-3.96 (m, 2H), 4.89 (s, 1H), 5.00 (s, 1H), 5.15-5.19 (m, 1H), 5.25-5.30 (m, 1H), 5.87-5.97 (m, 1H).

$^{13}$C NMR (100 MHz, CDCl$_3$): δ 12.6, 21.2, 28.5, 31.5, 69.5, 71.7, 109.8, 115.5, 133.5, 145.0.

Example 2

Synthesis of 2-((allyloxy)methyl)-3-methylbut-1-ene

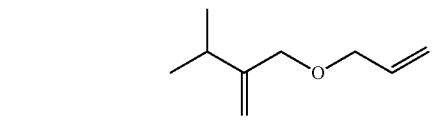

Step-1: Synthesis of 3-methyl-2-methylenebutanal:

3-Methylbutanal (391 g, 4.54 mol) was added to a mixture of aqueous 37% formaldehyde (368 g, 4.54 mol), di n-butylamine (30.0 g, 232 mmol) and p-anisic acid (35.0 g, 230 mmol) while stirring. Then the mixture was stirred at 70° C. for 1 h. Subsequently, the reaction mixture was cooled to 20° C. and aqueous saturated sodium hydrogen carbonate was added. The organic phase was separated and the crude product purified by distillation (105-106° C., 1 bar) to afford 3-methyl-2-methylenebutanal (53 g, 13%) as a colorless liquid.

Step-2: Synthesis of 3-methyl-2-methylenebutan-1-ol:

Sodium borohydride (800 mg, 21.1 mmol) was added portion wise to a mixture of 3-methyl-2-methylenebutanal (5.00 g, 50.9 mmol) in dichloromethane (3 mL) and methanol (6 mL) at 0° C. while stirring. Then, the reaction mixture was stirred at 0° C. for 15 min., followed by stirring at 20° C. for 2 h. Subsequently, aqueous 2 M hydrogen chloride was added until gas formation faded. Then, sodium chloride (2.40 g, 40.8 mmol) was added. The mixture was diluted with water and extracted with methyl tert-butyl ether. The organic phase was separated, washed with brine, dried over sodium sulfate and the volatiles were removed under reduced pressure (50° C., 400 mbar). The residue was distilled by bulb-to-bulb distillation to afford 3-methyl-2-methylenebutan-1-ol (2.4 g, 48%) as a colorless liquide.

Step-3: Synthesis of 2-((allyloxy)methyl)-3-methylbut-1-ene:

A suspension of sodium hydride 60% in mineral oil, (3.00 g, 75.0 mmol) was added portion wise to a solution of 3-methyl-2-methylenebutan-1-ol (5.00 g, 49.9 mmol) in tetrahydrofurane (50 mL) at 4° C. under nitrogen atmosphere. Then allyl bromide (12.1 g, 100 mmol) was added at 4° C. The reaction mixture was stirred at 20° C. for 3 days.

Then isopropanol (10 mL) was added followed by water (10 mL). The organic phase was separated and the aqueous phase was extracted with methyl tert-butyl ether (3×). The organic phases were combined and volatiles were removed under reduced pressure (50° C., 6 mbar). The residue (6.00 g) was purified by bulb-to-bulb distillation (110° C., 6 mbar) to afford 2-((allyloxy)methyl)-3-methylbut-1-ene (1.40 g, 20%) as a colorless liquid.

Example 3

Synthesis of 4-(allyloxy)-2-methyl-3-methylenehexane

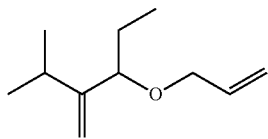

Step-1: Synthesis of 3-methyl-2-methylenebutanal:

3-Methylbutanal (200 g, 2.32 mol, 1 eq.) was added to a mixture of aqueous 37% formaldehyde (207 g, 2.55 mol, 1.1 eq.), di-n-butylamine (15.0 g, 116 mmol, 0.05 eq.) and p-anisic acid (17.6 g, 116 mmol, 0.05 eq.) at 25° C. over a period of 2 h and then the reaction mixture was heated at 70° C. for 4 h. The reaction mixture was cooled to 25° C. and the organic phase was separated, washed with water (3×100 mL) and dried over sodium sulfate (100 g). The crude mixture was distilled in vacuo (42-45° C./100 mbar) to afford 3-methyl-2-methylenebutanal (167 g, 73%) as a colorless liquid.

$^1$H NMR (400 MHz, CDCl$_3$): δ 1.01 (d, J=7.2 Hz, 6H), 2.69-2.76 (m, 1H), 5.89 (s, 1H), 6.18 (d, J=0.8 Hz, 1H), 9.46 (s, 1H).

$^{13}$C NMR (100 MHz, CDCl$_3$): δ 20.2, 24.2, 131.1, 155.6, 193.5.

Step-2: Synthesis of 5-methyl-4-methylenehexan-3-ol:

A solution of 3-methyl-2-methylenebutanal (100 g, 1.01 mol, 1 eq.) in tetrahydrofuran (500 mL) was added to a precooled (−5° C.) solution of ethyl magnesium chloride 2M in tetrahydrofurane (611 g, 1.22 mol, 1.21 eq.) at 5° C. over a period of 2 h while stirring. The reaction mixture was warmed to 25° C. over 3 h and then stirred at 25° C. for 4 h.

Subsequently, aqueous 40% ammonium chloride (250 mL) was added followed by methyl tert-butyl ether (300 mL) while stirring. Then, the organic phase was separated and aqueous phase was extracted with methyl tert-butyl ether (1×300 mL). Combined organic phases were washed with brine (100 mL) and dried over sodium sulfate (100 g). Volatiles were removed under reduced pressure and the residue was distilled in vacuo (45-50° C./7-10 mbar) to afford 5-methyl-4-methylenehexan-3-ol (70.5 g, 54%) as a colorless liquid.

$^1$H NMR (400 MHz, CDCl$_3$): δ 0.85 (t, J=7.6 Hz, 3H), 0.96 (d, J=5.6 Hz, 3H), 1.01 (d, J=7.2 Hz, 3H), 1.43-1.63 (m, 2H), 2.16-2.23 (m, 2H), 3.94-3.97 (m, 1H), 4.84 (s, 1H), 4.95 (s, 1H).

$^{13}$C NMR (100 MHz, CDCl$_3$): δ 8.3, 20.8, 20.9, 26.4, 28.3, 73.5, 105.3, 156.5.

Step-3: Synthesis of 4-(allyloxy)-2-methyl-3-methylenehexane:

Powdered potassium hydroxide (131 g, 2.33 mol, 2 eq.) was added to a mixture of 5-methyl-4-methylenehexan-3-ol (150 g, 1.17 mol, 1 eq.) and tetra-n-butyl ammonium bromide (18.7 g, 58.0 mmol, 50 meq.) at 25° C. over a period of 1 h while stirring. Then allyl chloride (224 g, 2.93 mol, 2.5 eq.) was added at 25-35° C. over a period of 2 h. The reaction mixture was stirred at 25° C. for 16 h. Subsequently, water (300 mL) was added followed by methyl tert-butyl ether (300 mL). Organic phase was separated, washed with water (3×300 mL) and dried over sodium sulfate (100 g). Volatiles were removed under reduced pressure. The residue was distilled in vacuo (52-59° C./7-13 mbar) to afford 4-(allyloxy)-2-methyl-3-methylenehexane (78.7 g, 40.0%) as a colorless liquid. GC purity=96%.

$^1$H NMR (400 MHz, CDCl$_3$): δ 0.82 (t, J=7.4 Hz, 3H), 0.96 (d, J=6.8 Hz, 3H), 1.00 (d, J=6.8 Hz, 3H), 1.47-1.54 (m, 2H), 2.13-2.20 (m, 1H), 3.53 (t, J=6.8 Hz, 1H), 3.65-3.71 (m, 1H), 3.89-3.94 (m, 1H), 4.90 (s, 2H), 5.05-5.08 (m, 1H), 5.15-5.21 (m, 1H), 5.78-5.84 (m, 1H).

$^{13}$C NMR (100 MHz, CDCl$_3$): δ 9.2, 21.6, 22.7, 26.0, 28.2, 68.0, 83.2, 108.6, 115.2, 134.3, 154.5.

Example 4

Synthesis of 2-(allyloxy)-4-methyl-3-methylenepentane

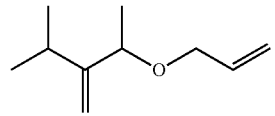

2-(allyloxy)-4-methyl-3-methylenepentane is prepared by following similar process steps as in example 3. For Step-2, MeMgCl was used instead of EtMgCl. Yield 28%

Example 5

Synthesis of 2-((allyloxy)methyl)hept-1-ene

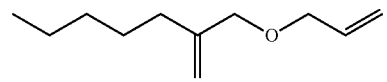

2-((allyloxy)methyl)hept-1-ene is prepared according to the procedure described in example 1. Yield 51%.

$^1$H NMR (600 MHz, CDCl$_3$): δ 0.89 (br. t, J=7.0 Hz, 3H), 1.26-1.35 (m, 4H), 1.45 (quint, J=7.4 Hz, 2H), 2.05 (t, J=7.7 Hz, 2H), 3.92 (s, 2H), 3.96 (d, J=5.5 Hz, 2H), 4.90 (s, 1H), 5.01 (s, 1H), 5.18 (d, J=10.4 Hz, 1H), 5.28 (br. d, J=17.2 Hz, 1H), 5.92 (ddt, J=17.1, 10.8, 5.6 Hz, 1H).

$^{13}$C NMR (600 MHz, CDCl$_3$): δ 14.1, 22.6, 27.3, 31.6, 33.1, 70.9, 73.0, 111.1, 116.8, 134.9, 146.3.

Example 6

Synthesis of 2-((allyloxy)methyl)oct-1-ene

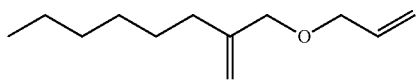

2-((allyloxy)methyl)oct-1-ene is prepared according to the procedure described in example 1. Yield 54%.

$^1$H NMR (600 MHz, CDCl$_3$): δ 0.89 (br. t, J=6.9 Hz, 3H), 1.29-1.47 (m, 6H), 1.44 (quint, J=7.7 Hz, 2H), 2.05 (t, J=7.7 Hz, 2H), 3.92 (s, 2H), 3.96 (br. d, J=5.6 Hz, 2H), 4.90 (s, 1H), 5.00 (s, 1H), 5.18 (dd, J=10.4, 1.5 Hz, 1H), 5.28 (br. dd, J=17.2, 1.7 Hz, 1H), 5.89-5.96 (m, 1H).

$^{13}$C NMR (600 MHz, CDCl$_3$): δ 14.1, 22.6, 27.6, 31.8, 33.2, 70.9, 73.0, 111.1, 116.8, 134.9, 146.3.

Example 7

Synthesis of 2-((allyloxy)methyl)undec-1-ene

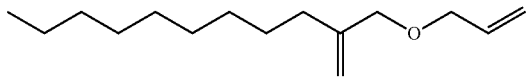 [SMILES: C=CCOCC(=C)CCCCCCCCC]

Step-1: Synthesis of 2-methylene-1-undecanal:

Undecanal (1.70 kg, 10.0 mol) was added to a mixture of aqueous 37% formaldehyde (892 g, 11 mol), diethanolamine (137 g, 1.30 mol) and boric acid (8.11 g, 130 mmol). The mixture was stirred at 80° C. for 6 h. Then the mixture was cooled to 20° C. and washed with aqueous 2M hydrochloric acid (80 mL), aqueous sodium hydrogen carbonate (80 mL), and brine (80 mL). The crude product was purified by distillation in vacuo (56-70° C./1 mbar) to afford 2-methylene-1-undecanal (1.50 kg, 82%) as a colorless liquid.

Step-3: 2-((allyloxy)methyl)undec-1-ene is prepared according to the procedure described in example 1. Yield 61%.

$^1$H NMR (600 MHz, CDCl$_3$): δ 0.89 (br. t, J=7.0 Hz, 3H), 1.20-1.35 (m, 12H), 1.40-150 (m, 2H), 2.05 (t, J=7.8 Hz, 2H), 3.91 (s, 2H), 3.96 (d, J=5.6 Hz, 2H), 4.89 (s, 1H), 5.00 (s, 1H), 5.23 (br. ddd, J=13.8, 11.8, 1.5 Hz, 2H), 5.89-5.96 (m, 1H).

$^{13}$C NMR (600 MHz, CDCl$_3$): δ 14.1, 22.7, 27.6, 29.3, 29.4, 29.5, 29.6, 31.9, 33.2, 70.9, 73.1, 111.1, 116.8, 134.9, 146.4.

Example 8

Synthesis of 2-((allyloxy)methyl)-3,7-dimethylocta-1,6-diene

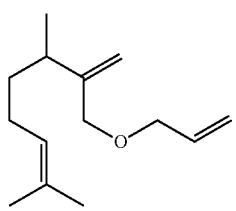

Step-1: Synthesis of 3,7-dimethyl-2-methyleneoct-6-enal:

Citronellal (344 g, 2.23 mol) was added to the mixture of paraformaldehyde (87.0 g, 2.90 mol), diethanolamine (16.4 g, 16.0 mmol) and benzoic acid (19.1 g, 16.0 mmol) while stirring. Then the mixture was stirred at 90° C. for 6 h. Subsequently, brine was added and the organic phase separated to afford the crude 3,7-dimethyl-2-methyleneoct-6-enal (398 g, 92%).

Step-2 and 3: Performed Like in Example 5.

$^1$H NMR (600 MHz, CDCl$_3$): δ 1.05 (d, J=6.9 Hz, 3H), 1.30-1.53 (m, 2H), 1.59 (s, 3H), 1.68 (s, 3H), 1.95 (br. q, J=7.5 Hz, 2H), 2.19 (sext, J=6.9 Hz, 1H), 3.94 (s, 2H), 3.97 (d, J=5.5 Hz, 2H), 4.91 (s, 1H), 5.05 (d, J=1.4 Hz, 1H), 5.09 (br. t, J=5.8 Hz, 1H), 5.18 (br. dd, J=10.4, 1.4 Hz, 1H), 5.28 (br. dd, J=17.2, 1.6 Hz, 1H), 5.89-5.96 (m, 1H).

$^{13}$C NMR (600 MHz, CDCl$_3$): δ 17.7, 19.9, 25.7, 25.9, 35.7, 36.5, 71.0, 72.0, 110.0, 116.8, 124.6, 131.4, 134.9, 150.9.

The olfactory properties of the above compounds are given in the below table

| Compounds of formula (I) | Olfactory notes |
|---|---|
| Example 1: R$_1$ = n-Bu, R$_2$ = H | very diffusive, green, fruity, pear |
| Example 2: R$_1$ = i-Pr, R$_2$ = H | diffusive, herbaceous, thyme, slightly sweet, camphoraceous, phenolic |
| Example 3: R$_1$ = i-Pr, R$_2$ = Et | diffusive, slightly cooling, mint/green/herbal |
| Example 4: R$_1$ = i-Pr, R$_2$ = Me | diffusive, conifer, fruity, slightly sweet |
| Example 5: R$_1$ = n-Pentyl, R$_2$ = H | fruity, floral, green/herbal |
| Example 6: R$_1$ = n-Hex, R$_2$ = H | Fruity, pear, waxy, green, very natural, slightly sweet, ripe conference pear |
| Example 7: R$_1$ = n-C$_9$H$_{19}$, R$_2$ = H | Fruity, tutti frutti, citrus, sweet, slightly dry fatty |
| Example 8: 2-((allyloxy)methyl)-3, 7-dimethylocta-1,6-diene | Etheral, green, slightly floral, fruity, pear, direction pear ester |

The disclosure is further illustrated by the following examples which in no way should be construed as being further limiting. One skilled in the art will readily appreciate that the specific methods and results described are merely illustrative.

Examples 9 to 11

In the following examples 9 to 11, the compound of example 1 was included in 3 different compositions. Olfactory evaluations were made from a shower gel, dosed at 0.3 wt % perfume composition.

Examples 9 and comparative 9—Spicy composition

|  | Ex. C9 Parts | Ex. 9 Parts |
|---|---|---|
| Clove Oil Rectified | 315 | 315 |
| Cinnamic Aldehyde | 280 | 280 |
| Cinnamyl Nitrile | 200 | 200 |
| *Litsea Cubeba* Terpenes | 70 | 70 |
| Nutmeg Oil | 15 | 15 |
| Benzaldehyde | 12 | 12 |
| Ethyl Maltol | 5 | 5 |
| Methyl Octalactone PFW | 3 | 3 |
| Example 1 compound | 0 | 30 |
| DPG | 100 | 70 |
| Total Parts | 1000 | 1000 |

The addition of 3.0 wt % of the example 1 compound rendered the spicy composition significantly more performant and diffusive, accentuating the natural cinnamon character and rounding the harsh nitrile aspect. Additionally, a fresh, fruity character was introduced that integrated the various spice characters in the mixture.

Examples 10 and comparative example 10—Fougere Composition:

|  | Ex. C10 Parts | Ex. 10 Parts |
| --- | --- | --- |
| Phenylethyl Alcohol | 270 | 270 |
| Geraniol 80/20 | 190 | 190 |
| Kflorol 90 PFW | 150 | 150 |
| Tonalid PFW | 80 | 80 |
| Coumarin | 75 | 75 |
| Lavendin Grosso Oil | 70 | 70 |
| Benzyl Acetate | 55 | 55 |
| Verotyl PFW | 10 | 10 |
| Example 1 compound | 0 | 5 |
| DPG | 100 | 95 |
| Total | 1000 | 1000 |

Adding only 0.5 wt % of the example 1 compound to the fougere composition boosted the performance and diffusivity of the composition, blending seamlessly to soften the camphoraceous character of the Lavendin Grosso Oil. The complexity of the composition was significantly enhanced. While the fruity/green character of the target was not specifically apparent the freshness and "clean" impression of the composition was greatly enhanced.

Examples 11 and comparative example 11—Citrus Composition:

|  | Ex. C11 Parts | Ex. 11 Parts |
| --- | --- | --- |
| Orange Oil Cold Pressed | 560 | 560 |
| Litsea Cubeba Terpenes | 180 | 180 |
| Citronellyl Nitrile | 64 | 64 |
| para-tertiary Butyl Cyclohexyl Acetate | 50 | 50 |
| Aldehyde C10 | 40 | 40 |
| Ethyl Maltol | 2.5 | 2.5 |
| trans-2-Dodecenal | 2 | 2 |
| Delta Damascone | 1.5 | 1.5 |
| Example 1 compound | 0 | 30 |
| DPG | 100 | 70 |
| Total | 1000 | 1000 |

An "overdose" of 3.0 wt % of the example 1 compound shifts the olfactory profile of the composition significantly, transforming it from an orange/lemon character to a bitter green lime, directionally kaffir lime leaf with grapefruit aspects. Additionally, the performance of the already strong composition increased significantly and in unanticipated manner, with the green character of the target interacting synergistically with the trans-2-dodecenal and the Litsea Cubeba Terpenes.

The invention claimed is:

1. Fragrance, flavor and/or deodorizing/masking composition comprising at least one 2- and/or 3-substituted 3-(allyloxy)propene of formula (I)

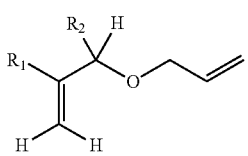

(I)

wherein $R_1$ is either an alkyl group having up to 9 carbon atoms or an alkenyl group having up to 9 carbon atoms and $R_2$ is hydrogen or an alkyl or alkenyl group having up to 5 carbon atoms.

2. Fragrance, flavor and/or deodorizing/masking composition according to claim 1 wherein $R_1$ is an alkyl group having up to 5 carbon atoms.

3. Fragrance, flavor and/or deodorizing/masking composition according to claim 1 wherein the 2- and/or 3-substituted 3-(allyloxy)propene of formula (I) does not include the compound of formula (I) having a methyl group as $R_1$ and hydrogen as $R_2$.

4. Fragrance, flavor and/or deodorizing/masking composition according to claim 1 wherein the 2- and/or 3-substituted 3-(allyloxy)propene of formula (I) comprises at least 8 carbon atoms.

5. Fragrance, flavor and/or deodorizing/masking composition according to claim 1 wherein $R_1$ is an alkyl group having at least 2 carbon atoms.

6. Fragrance, flavor and/or deodorizing/masking composition according to claim 1 wherein the compound of formula (I) is selected from 2-((allyloxy)methyl)hex-1-ene, 2-((allyloxy)methyl)-3-methylbut-1-ene, 2-(allyloxy)-4-methyl-3-methylenepentane, 4-(allyloxy)-2-methyl-3-methylenehexane, 2-((allyloxy)methyl)hept-1-ene, 2-((allyloxy)methyl)oct-1-ene, 2-((allyloxy)methyl)undec-1-ene, or 2-((allyloxy)methyl)-3,7-dimethylocta-1,6-diene.

7. Fragrance, flavor and/or deodorizing/masking composition according to claim 1 wherein the compound of formula (I) is 2-((allyloxy)methyl)hex-1-ene.

8. Fragrance, flavor and/or deodorizing/masking composition according to claim 1 wherein the content of the compound of formula (I) is comprised between 0.0001 and 95 wt %.

9. Fragrance, flavor and/or deodorizing/masking composition according to claim 1 further comprising at least one ester and/or one alcohol.

10. Fragrance, flavor and/or deodorizing/masking composition according to claim 9 wherein the total content in the composition of the compound(s) of formula (I) together with the ester(s) and/or alcohol(s) is greater than 25 wt %.

11. Fragrance, flavor and/or deodorizing/masking composition according to claim 9, wherein the total content in the composition of the compound(s) of formula (I) together with the ester(s) and/or alcohol(s) is greater than 50 wt %.

12. Fragrance, flavor and/or deodorizing/masking composition according to claim 9, wherein the total content in the composition of the compound(s) of formula (I) together with the ester(s) and/or alcohol(s) is greater than 75 wt %.

13. Fragrance, flavor and/or deodorizing/masking composition according to claim 9, wherein the total content in the composition of the compound(s) of formula (I) together with the ester(s) and/or alcohol(s) is greater than 90 wt %.

14. Fragrance, flavor and/or deodorizing/masking composition according to claim 9, further comprising at least a mixture of ester and alcohol.

15. Fragrance, flavor and/or deodorizing/masking composition according to claim 1 wherein $R_1$ is an alkyl group having 4 carbon atoms and $R_2$ is hydrogen or an alkyl or alkenyl group having up to 5 carbon atoms.

16. Fragrance, flavor and/or deodorizing/masking composition according to claim 1 wherein $R_1$ is an alkyl group having 4 carbon atoms and $R_2$ is hydrogen or an alkyl or alkenyl group having up to 5 carbon atoms, with the proviso that when $R_2$ is hydrogen, $R_1$ is not tert-butyl.

* * * * *